US011851685B2

United States Patent
Carrington et al.

(10) Patent No.: US 11,851,685 B2
(45) Date of Patent: Dec. 26, 2023

(54) ZWITTERION BUFFER CONTAINING COMPOSITIONS AND USES IN ELECTROANALYTICAL DEVICES AND METHODS

(71) Applicant: ROCHE DIABETES CARE, INC., Indianapolis, IN (US)

(72) Inventors: Nathan Allen Carrington, Noblesville, IN (US); Stacy Hunt Duvall, Indianapolis, IN (US); Leon Scott Van Dyke, Fishers, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 17/520,999

(22) Filed: Nov. 8, 2021

(65) Prior Publication Data

US 2022/0275348 A1 Sep. 1, 2022

Related U.S. Application Data

(63) Continuation of application No. 16/289,933, filed on Mar. 1, 2019, now abandoned, which is a (Continued)

(51) Int. Cl.
| | |
|---|---|
| *C12Q 1/00* | (2006.01) |
| *G01N 27/327* | (2006.01) |
| *C12N 9/04* | (2006.01) |
| *C12Q 1/54* | (2006.01) |
| *C12Q 1/32* | (2006.01) |
| *C12Q 1/26* | (2006.01) |

(52) U.S. Cl.
CPC .......... *C12N 9/0006* (2013.01); *C12Q 1/006* (2013.01); *C12Q 1/26* (2013.01); *C12Q 1/32* (2013.01); *C12Q 1/54* (2013.01); *G01N 27/3271* (2013.01)

(58) Field of Classification Search
CPC ........ C12N 9/0006; C12Q 1/006; C12Q 1/26; C12Q 1/32; C12Q 1/54; G01N 27/327; G01N 27/3271; G01N 27/3272
See application file for complete search history.

(56) References Cited

U.S. PATENT DOCUMENTS 5,243,516 A * 9/1993 White ............... G01N 27/3273
435/287.2
5,286,362 A * 2/1994 Hoenes ................. C12Q 1/004
435/817
(Continued)

FOREIGN PATENT DOCUMENTS

WO WO 9917115 A1 * 4/1999 ........... G01N 33/487
WO 2001021827 3/2001

OTHER PUBLICATIONS

MES description in the TargetMol® catalog, downloaded Feb. 9, 2023 from https://www.targetmol.com/compound/mes (Year: 2022).*
(Continued)

*Primary Examiner* — Alexander S Noguerola
(74) *Attorney, Agent, or Firm* — Brannon Sowers & Cracraft PC

(57) ABSTRACT

Described herein are reagent compositions for detecting and/or measuring analytes in a test sample. In one embodiment, reagent compositions are described for detecting and/or measuring glucose in a sample.

20 Claims, 7 Drawing Sheets

Related U.S. Application Data continuation of application No. 13/805,186, filed as application No. PCT/EP2011/003656 on Jul. 21, 2011, now abandoned.

(60) Provisional application No. 61/367,243, filed on Jul. 23, 2010.

(56) References Cited

U.S. PATENT DOCUMENTS

| | | | |
|---|---|---|---|
| 5,403,691 A * | 4/1995 | Oshiba | G03G 5/06147 430/72 |
| 5,527,509 A | 6/1996 | Gibson | |
| 5,846,702 A * | 12/1998 | Deng | C07F 15/0026 435/14 |
| 6,270,637 B1 * | 8/2001 | Crismore | G01N 33/5438 204/403.14 |
| 7,776,575 B2 | 8/2010 | Yamoaka et al. | |
| 2003/0104595 A1 * | 6/2003 | Kratzch | C12N 9/0006 435/189 |
| 2004/0050717 A1 | 3/2004 | Teodorczyk | |
| 2005/0019212 A1 | 1/2005 | Bhullar et al. | |
| 2006/0180479 A1 | 8/2006 | Sparkes et al. | |
| 2007/0053790 A1 | 3/2007 | Nagakawa | |
| 2007/0080073 A1 * | 4/2007 | Wu | C12Q 1/006 204/403.01 |
| 2007/0105173 A1 | 5/2007 | Takeshima | |
| 2008/0248514 A1 | 10/2008 | Inamori et al. | |

OTHER PUBLICATIONS

Sari et al., "Polystyrene Attached Pt(IV)-Azomethine, Synthesis and Immobilization of Glucose Enzyme," Int. J. Mol. Sci. 2012, 13, 11870-11880 (Year: 2012).*

Pongharangkul et al., "Kinetic properties and stability of glucose dehydrogenase from Bacillus amyloliquefaciens SB5 and its potential for cofactor regeneration," AMB Expr (2015) 5:68 DOI 10.1186/s13568-015-0157-9, 12 pages (Year: 2015).*

Iswantini, D., Kenji, K. A. N. O., & Ikeda, T. (2000). Kinetics and thermodynamics of activation of quinoprotein glucose dehydrogenase apoenzyme in vivo and catalytic activity of the activated enzyme in *Escherichia coli* cells. Biochemical Journal, 350(3), 917-923.

Olsthoorn, A. J., & Duine, J. A. (1996). Production, Characterization, and Reconstitution of Recombinant Quinoprotein Glucose Dehydrogenase (Soluble Type; EC 1.1. 99.17) Apoenzyme ofAcinetobacter calcoaceticus. Archives of biochemistry and biophysics, 336(1), 42-48.

PCT Search Report and Written Opinion for PCT/EP2011/003656, completed Sep. 23, 2011.

Bankar, S. B., Bule, M. V., Singhal, R. S., & Ananthanarayan, L. (2009). Glucose oxidase—an overview. Biotechnology advances, 27(4), 489-501.

Oliver, N. S., Toumazou, C., Cass, A. E. G., & Johnston, D. G. (2009). Glucose sensors: a review of current and emerging technology. Diabetic Medicine, 26(3), 197-210.

Seker, S., & Becerik, I. (2004). A neural network model in the calibration of glucose sensor based on the Immobilization of glucose oxidase into polypyrrole matrix. Electroanalysis: An International Journal Devoted to Fundamental and Practical Aspects of Electroanalysis, 16(18), 1542-1549.

Bonitz-Diulat, M. (2006). Design of Tailor-made Enzymes for Blood Glucose Detection. Chemie Ingenieur Technik, 78(9), 1407.

* cited by examiner

Fig. 7

Bias of High Glucose DC Response
(%, 45°C vs. 4°C)

Weeks of Exposure

ZWITTERION BUFFER CONTAINING COMPOSITIONS AND USES IN ELECTROANALYTICAL DEVICES AND METHODS

CROSS-REFERENCE TO RELATED APPLICATIONS

This application is a continuation of U.S. patent application Ser. No. 16/289,933, filed Mar. 1, 2019, which is a continuation of U.S. patent application Ser. No. 13/805,186, filed Dec. 18, 2012, which is a U.S. national application under 37 C.F.R. § 371(b) of International Application Serial No. PCT/EP2011/003656 filed Jul. 21, 2011, which claims priority to U.S. Provisional Application Ser. No. 61/367,243, filed Jul. 23, 2010. The entirety of the disclosures of the foregoing applications are incorporated herein by reference.

TECHNICAL FIELD

The invention described herein pertains to compositions, devices, and uses in the analytical detection and/or quantification of an analyte. In particular, the invention pertains to electroanalytical detection and/or quantification of glucose.

BACKGROUND AND SUMMARY OF THE INVENTION

Monitoring the concentration of biologically significant compounds for the early detection and treatment of health risks has been developed into a robust field of development which has improved the health of mankind. Those biologically significant compounds targeted for analysis by a particular technology are called analytes. Of significant importance to human health is the monitoring of glucose within intravascular blood. Blood glucose analysis has been so broadly adopted and the technology so significantly advanced that individuals can personally test their own blood. The quantification of that blood glucose concentration has become an important component of persons managing their own health. In particular, the information can be used to assist in the determination of the appropriate dosages of insulin for diabetics, under the direction of a physician.

One of the methods developed for monitoring blood glucose concentrations has been the use of electrochemical biosensors. Electrochemical biosensors are primarily based on enzyme-catalyzed chemical reactions involving the analyte of interest. In the case of glucose monitoring, the relevant chemical reaction is the oxidation of glucose to gluconolactone. This oxidation is catalyzed by a variety of enzymes, some of which may contain a bound coenzyme such as nicotinamide adenine dinucleotide (phosphate) (NAD(P)), while others may contain a bound cofactor such as flavin adenine dinucleotide (FAD) or pyrroloquinolinequinone (PQQ).

One type of a electrochemical biosensor uses a disposable test strip that includes the required electrical cell (electrodes), the chemical reagents, and a chamber for depositing a sample. A variety of test strips are used to measure glucose concentrations in blood to monitor the blood sugar level of people with diabetes. More specifically, these test strips include a reaction chamber into which a reagent composition has been deposited. The reagent compositions used within the test strip can and have varied substantially. In one class of test strips, the reagents are deposited within the test strip as a thin, uniform, dried film or layer. As a sample is introduced into the chamber of the test strip, the reagent composition is rehydrated into the sample so that the reagents can react with the analyte. Reactions between the reagents and the analyte result in the electrochemical properties of the solution changing. This change in properties can be monitored using an electronic device that is designed to read the test strip. It is to be understood that a wide variety of conventional devices may be used to read the test-strips described herein.

It has been surprisingly discovered herein that zwitterionic buffers may be included in a wide variety of reagent systems, and may improve the kinetics of glucose detection and/or measurement. In particular, it has been discovered that zwitterionic buffers may improve time to maximum signal and/or improve the magnitude of the maximum signal compared to other buffers. It is appreciated that such a shorter time to maximum signal may allow the DC response to stabilize more quickly, and lead to improved precision compared to other buffers that more slowly reach the DC response maximum. Without being bound by theory, it is believed herein that zwitterionic buffers may increase the overall rate of the enzymatic reaction with glucose. Without being bound by theory, it is believed herein that the increased reaction rate of FAD-GDH with glucose may allow for the use of test sequences with shorter incubation times.

It has also been surprisingly discovered herein that zwitterionic buffers may improve the stability, such as the storage stability, of reagent compositions useful for glucose detection and/or measurement. In particular, it has been discovered that zwitterionic buffers may improve the temperature stability of the reagent composition. It has also been surprisingly discovered herein that zwitterionic buffers may lead to an overall decrease in sodium interference.

In one illustrative embodiment of the invention, a reagent composition is described. In one aspect, the reagent composition is useful for detecting and/or measuring glucose in a sample. In another aspect, the reagent composition includes one or more enzymes for detecting glucose, such as one or more glucose dehydrogenases, one or more glucose oxidoreductases, and combinations thereof. In another aspect, the reagent composition includes one or more co-factors, co-enzymes, or a combination thereof for the one or more enzymes. In another aspect, the reagent composition includes one or more mediators, mediator precursors, or a combination thereof. In another aspect, the reagent composition includes one or more zwitterionic buffers. In another embodiment, the reagent composition also includes one or more adjuvants. It is to be understood that the reagent composition may be configured in any of a variety of formats, including formats described herein such as a dried reagent composition on a test strip.

In another embodiment, methods for detecting and/or measuring glucose in a sample are described. The methods include the step of contacting a sample containing glucose with a reagent composition described herein.

In another embodiment, electrochemical sensors for detecting and/or measuring glucose in a sample are described. The electrochemical sensors include a reagent composition described herein.

In another embodiment, devices for detecting and/or measuring glucose in a sample are described. The devices include a component comprising a reagent composition described herein.

BRIEF DESCRIPTION OF THE DRAWINGS

FIG. 7 shows the high glucose stability response versus exposure time of illustrative sensors based on FAD-GDH strips including a PIPES buffer (squares) and a phosphate buffer (diamonds).

DETAILED DESCRIPTION

Figure 1:
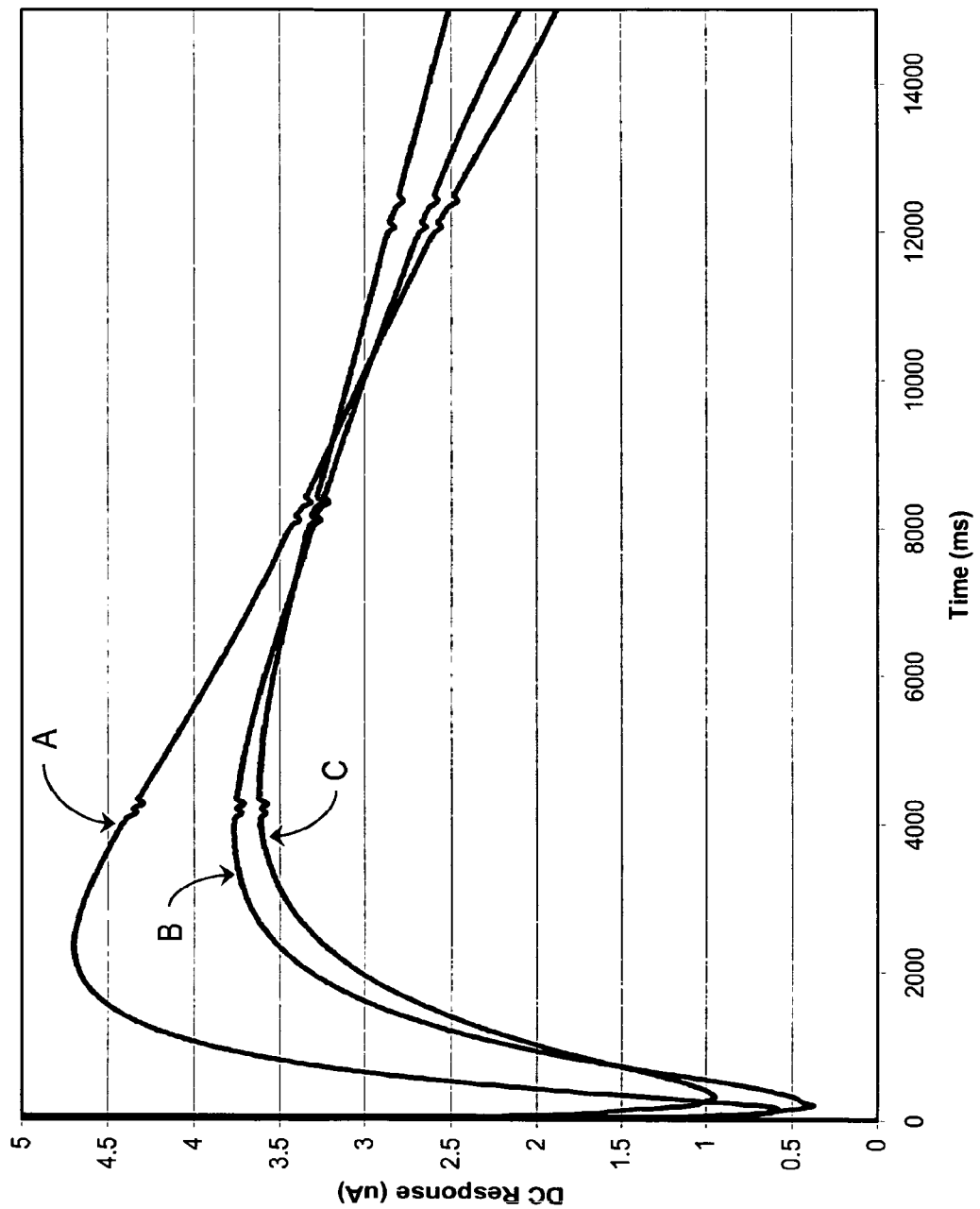
FIG. 1 shows the kinetics curves for DC response (µA) versus time (ms) for three illustrative sensors based on a PQQ-GDH enzyme using reagents that include (A) a PIPES buffer, (B) a β-glycerophosphate buffer, and (C) a phosphate buffer.

In another embodiment, a reagent composition is described herein. In one aspect, the reagent composition may be used to detect and/or measure glucose in a sample. The reagent composition comprises one or more enzymes, such as one or more glucose dehydrogenases, one or more glucose oxidoreductases, and combinations thereof; (b) one or more co-factors, co-enzymes, or a combination thereof for the one or more enzymes; (c) one or more mediators, mediator precursors, or a combination thereof; and (d) one or more zwitterionic buffers.

In another embodiment, the zwitterionic buffer is an aminoalkanoic acid buffer. In another embodiment, the zwitterionic buffer is an aminoalkylsulfonic acid buffer. Illustrative zwitterionic buffers include, but are not limited to, 2-(N-morpholino)ethanesulfonic acid (MES), piperazine-N,N'-bis(2-ethanesulfonic acid) (PIPES), N-(2-Acetamido)-2-aminoethanesulfonic acid (ACES), (4-(2-hydroxyethyl)-1-piperazineethanesulfonic acid) (HEPES), N-(Tri(hydroxymethyl)methyl)glycine (tricine), N,N-Bis(2-hydroxyethyl)glycine; (bicine), 3-(N-morpholino)propanesulfonic acid (MOPS), N-cyclohexyl-3-aminopropanesulfonic acid (CAPS), N,N-Bis(2-hydroxyethyl)-2-aminoethanesulfonic Acid (BES), N-(Hydroxyethyl)piperazine-N'-2-hydroxypropanesulfonic acid (HEPPSO).

In another embodiment, the zwitterionic buffer is PIPES. In another embodiment, the zwitterionic buffer is MOPS.

Illustrative co-factors and co-enzymes include, but are not limited to, pyrroloquinoline quinone (PQQ), nicotine adenine dinucleotide (NAD, such as in glucose dehydrogenase nicotine adenine dinucleotide (GDH-NAD), flavin adenine dinucleotide (FAD), such as in flavin adenine dinucleotide glucose dehydrogenase (FAD-GDH), and the like. It is appreciated that wild forms (including naturally occurring forms) and mutant forms (including synthetically prepared forms) of such enzymes, enzyme-cofactors, and co-enzymes may be included in the reagent compositions described herein.

Enzymes useful for glucose analysis in electrochemical systems include oxidoreductases, such as glucose oxidases (GODs), glucose dehydrogenase (GDHs), which may also be referred to as glucose de-oxidoreductase (GlucDORs), and the like. Illustrative glucose dehydrogenases (GDHs) include, but are not limited to, wild-type GDHs, mutant GDHs, and the like. In another illustrative embodiment, the enzyme is a mutant GDH that is less sensitive to, or insensitive to maltose. It is to be understood that co-enzymes, such as GDH-NADs, FAD-GDHs, and the like, may be included in the reagent compositions described herein. Additional illustrative enzymes are described in U.S. Pat. Application Publication No. http://patft.uspto.gov/netacgi/nph-Parser?Sect1=PTO1&Sect2=HITOFF&d=PALL&p=1&u=%2Fnetahtml%2FPTO%2Fsrchnum.htm&r=1&f=G&1=50&s1=7163616.PN.&OS=PN/7163616&RS=PN/7163616-h0#h0http://patft.uspto.gov/netacgi/nph-Parser?Sect1=PTO1&Sect2=HITOFF&d=PALL&p=1&u=%2Fnetahtml%2FPTO%2Fsrchnum.htm&r=1&f=G&1=50&s1=7163616.PN.&OS=PN/7163616&RS=PN/7163616-h2#22008/0248514, and U.S. Pat. No. 7,732,179, the disclosures of which are incorporated herein by reference. In another illustrative embodiment, the enzyme is a mutant GDH that is more thermally stable.

Additional illustrative mutant PQQ-GDH enzymes, including mutant PQQ-GDH enzymes exhibiting maltose insensitivity, are described in U.S. Pat. Nos. 7,547,535; 7,547,524; and 7,732,179, the disclosures of which are incorporated herein by reference.

Additional illustrative co-enzymes, such as FAD-GDH coenzymes are described in U.S. Pat. No. 7,662,600, the disclosure of which is incorporated herein by reference.

Mediators and mediator precursors are typically provided in the reagent composition in order to facilitate transfer of electrons during a desired chain of oxidation-reduction reactions that ultimately produce an electroactive species. The electroactive species, when measured, serves to indicate the desired electrochemical analysis result, such as presence or concentration of a target analyte. A mediator generally is a compound that participates in the chain of such electron exchange reactions in the form provided in the reagent composition, typically in a reversible oxidized or reduced state. A mediator precursor, on the other hand, is a compound that as provided in the reagent composition must itself undergo one or more side reactions after the reagent composition comes into contact with a fluid sample in order to produce a form of a mediator compound capable of participating in the electron exchange reactions. Typically, the one or more side reactions are not reversible, such that once the mediator compound is formed, it cannot return to the form of the mediator precursor. The most common families of mediators and mediator precursors include, for example, benzoquinones, transition metal complexes (e.g. potassium ferricyanide), osmium derivatives (e.g., osmium bipyridyl complexes), and nitrosoaniline derivatives. Specific illustrative mediators and mediator precursors include, but are not limited to, N,N'-bis-(2-hydroxyethyl)-p-nitrosoaniline, N,N'-dimethyl-p-nitrosoaniline, N,N'-diethyl-p-nitrosoaniline, N-methyl-N'-(4-nitrosophenyl)-piperazine, N-(2-hydroxyethyl)-5-nitrosoindoline, 2,4-dimethoxy-nitrosobenzene, N,N'-bis-(2-methoxyethyl)-4-nitrosoaniline, N-(4-n itrosophenyl)-morpholine, N-(2,2-diethoxy-ethyl)N'-(4-nitrosophenyl)-piperazine, p-nitrosophenol, 3-methoxy-4-nitrosophenol.

Further illustrative mediators and mediator precursors include, but are not limited to, N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniiine, 3-methoxy-4-nitrosophenol, N-(2-hydroxyethyl)-6-nitroso-1,2,3,tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoaniline.

Further illustrative mediators and mediator precursors include, but are not limited to, 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxy-carbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2"-(5"'-(p-aminophenyl)-1,3,4-oxadiazoyl)phenylimino)-3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, 3-(3-phenylimino)-3H-phenothiazinesulfonic acid, and combinations thereof.

Additional illustrative mediators and mediator precursors are described in U.S. Pat. Nos. http://patft.uspto.gov/netacgi/nph-Parser?Sect1=PTO1&Sect2=HITOFF&d=PALL&p=1&u=%2Fnetahtml%2FPTO%2Fsrchnu m.htm&r=1&f=G&l=50&s1=5,122, 244.PN.&OS=PN/5,122,244&RS=PN/5,122,244-h0#h0http://patfluspto.gov/netacgi/nph-Parser?Sect1=PTO1&Sect2=HITOFF&d=PALL&p=1&u=%2Fnetahtml%2FPTO%2Fsrchnu m.htm&r=1&f=G&l=50&s1=5,122,244.PN.&OS=PN/5, 122,244&RS=PN/5,122,244-h2#H25,122,244, 5,286,362, 5,858,691, and http://patft.uspto.gov/netacgi/nph-Parser?Sect1=PTO1&Sect2=HITOFF&d-PALL&p=1&u=%2Fnetahtml%2FPTO%2Fsrchnu m.htm&r=1&f=G&l=50&s1=7163616.PN.&OS=PN/ 7163616&RS=PN/7163616-h0#h0http://patit.uspto.gov/netacgi/nph-Parser?Sect1=PTO1&Sect2=HITOFF&d=PALL&p=1&u=%2Fnetahtml%2FPTO%2Fsrchnum. htm&r=1&f=G&l=50&s1=7163616.PN.&OS=PN/ 7163616&RS=PN/7163616-h2#h27,163,616, and WO 98/35225, the disclosures of which are incorporated herein by reference. Processes for preparing mediators described herein are also described in U.S. Pat. No. http://patft.upspto.gov/netacgi/nph-Parser?Sect1=PTO1&Sect2=HITOFF&d=PALL&p=1&u=%2Fnetahtml%2FPTO%2Fsrchnum. htm&r=1&f=G&l=50&s1=5,122,244. PN.&OS=PN/5,122, 244&RS=PN/5,122,244-h0#h0http://patft.uspto.gov/netacgi/nph-Parser?Sect1=PTO1&Sect2=HITOFF&d=PALL&p=1&u=%2Fnetahtml&2FPTO%2Fsrchnum. htm&r=1&f=G&l=50&s1=5,122,244.PN.&OS=PN/5,122, 244&RS=PN/5,122,244-h2#h25,122,244.

In another embodiment, the reagent compositions described herein include one or more additional buffers. Illustrative buffers include, but are not limited to, phosphoric acid, beta-glycerophosphoric acid, and the like, and including salts, hydrates, and/or solvates of the foregoing.

The reagent composition may also include a variety of adjuvants to enhance the reagent properties or characteristics. For example, the composition may include adjunct materials to facilitate the placement of the reagent composition onto the test strip and to improve its adherence to the strip. The composition can also include materials to increase its rate of hydration and/or its increase its influence on the capillary action to fill the chamber with the test sample. Additionally, the reagent composition can include components selected to enhance the physical properties of the resulting dried reagent composition, and the uptake of a liquid test sample for analysis. Examples of adjuvant materials to be used with the reagent composition include thickeners, viscosity modulators, film formers, stabilizers, buffers, detergents, gelling agents, fillers, film opening agents, coloring agents, and agents endowing thixotropy. The adjuvant materials or components can impact the application, reproducibility and physical properties of the reagent composition.

In another embodiment, the reagent compositions described herein include one or more film forming and/or thixotropic agents, and/or dispersants. Illustrative film forming and/or thixotropic agents, and/or dispersants include, but are not limited to, silicas, such as Kieselsure Sipemate FK 320 DS by Degussa AG, polyvinylpyrrolidones, polyvinyl propionate dispersion, and the like, and including salts, hydrates, and/or solvates of the foregoing.

In another embodiment, the reagent compositions described herein include one or more viscosity modulators or viscosity adjusting agents. Illustrative viscosity adjusting agents include, but are not limited to, polysaccharides, starches, and gums, such as pectin, guar gum, locust bean (carob seed) gum, konjac gum, xanthan gum, alginates, and agar, casein, gelatin, and phycocolloids; cellulose and semisynthetic cellulose derivatives (carboxymethyl-cellulose, methyl cellulose, hydroxymethylcellulose, hydroxyethylcellulose, methylhydroxyethylcellulose), such as, xanthan gums, such as Keltrol F by CP Kelco US, Inc., carboxymethyl cellulose, such as AQUALON.®.CMC 7F PH by Hercules Inc., Aqualon Division; polyvinyl alcohol and carboxy-vinylates; bentonite, silicates, and colloidal silica, and the like, and including salts, hydrates, and/or solvates of the foregoing.

In another embodiment, the reagent compositions described herein include one or more stabilizers. Illustrative stabilizers include, but are not limited to, calcium chloride, saccharides, such as trehalose, such as D-(+)-Trehalose dihydrate by Sigma Chemical Co., mono- or di-fatty acids, poly carboxylic acids, such as sodium succinate, and the like, and including salts, hydrates, and/or solvates of the foregoing.

In another embodiment, the reagent compositions described herein include one or more detergents and/or surfactants. Illustrative detergents and/or surfactants include, but are not limited to, water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. Illustrative detergents for the present invention include an ester amide, n-octanoyl-N-methylglucamide, sold under the trade name Mega-8 by Dojindo Molecular Technologies, Inc., and a fatty acid salt, N-methyl oleyl taurate sodium salt, such as Geropon T77 by Rhodia HPCII (Home, Personal Care and Industrial Ingredients).

In another embodiment, the reagent compositions described herein include one or more pH adjusting agents. Illustrative pH adjusting agents include, but are not limited to, acids, such as mineral acids including hydrochloric acid, sulfuric acid, and the like; bases, such as sodium hydroxide, potassium hydroxide, sodium bicarbonate, sodium carbonate, potassium carbonate, and the like.

It is to be understood that all possible combinations of each of the foregoing embodiments are described herein without limitation. For example, the foregoing description is to be understood to include illustrative reagent compositions comprising PQQ-GDH enzymes, including mutant PQQ-GDH enzymes, and PIPES. Additional illustrative reagent compositions comprise PQQ-GDH enzymes, including mutant PQQ-GDH enzymes, PIPES, and one or more mediators or mediator precursors, such as one or more nitrosoanilines, and the like. Additional illustrative reagent compositions comprise PQQ-GDH enzymes, including mutant PQQ-GDH enzymes, PIPES, and one or more film forming reagents, such as one or more polyvinyl acetate propionate co-polymers, polyvinyl propionate dispersions, polyvinylpyrrolidones, and the like. Additional illustrative reagent compositions comprise PQQ-GDH enzymes, including mutant PQQ-GDH enzymes, PIPES, and one or more viscosity modifying agents, such as one or more semi-synthetic cellulose derivatives, such as hydroxyethylcellulose, and the like. Additional illustrative reagent compositions comprise PQQ-GDH enzymes, including mutant PQQ-GDH enzymes, PIPES, one or more film forming reagents, such as one or more polyvinyl acetate propionate co-polymers, polyvinyl propionate dispersions, polyvinylpyrrolidones, and the like, and one or more viscosity modifying agents, such as one or more semi-synthetic cellulose derivatives, such as hydroxyethylcellulose, and the like. Additional illustrative reagent compositions comprise PQQ-GDH enzymes, including mutant PQQ-GDH enzymes, and MOPS. Additional illustrative reagent compositions comprise PQQ-GDH enzymes, including mutant PQQ-GDH enzymes, MOPS, and one or more mediators or mediator precursors, such as one or more nitrosoanilines, and the like. Additional illustrative reagent compositions comprise PQQ-GDH enzymes, including mutant PQQ-GDH enzymes, MOPS, and one or more film forming reagents, such as one or more polyvinyl acetate propionate co-polymers, polyvinyl propionate dispersions, polyvinylpyrrolidones, and the like. Additional illustrative reagent compositions comprise PQQ-GDH enzymes, including mutant PQQ-GDH enzymes, MOPS, and one or more viscosity modifying agents, such as one or more semi-synthetic cellulose derivatives, such as hydroxyethylcellulose, and the like. Additional illustrative reagent compositions comprise PQQ-GDH enzymes, including mutant PQQ-GDH enzymes, MOPS, one or more film forming reagents, such as one or more polyvinyl acetate propionate co-polymers, polyvinyl propionate dispersions, polyvinylpyrrolidones, and the like, and one or more viscosity modifying agents, such as one or more semi-synthetic cellulose derivatives, such as hydroxyethylcellulose, and the like. The foregoing are illustrative of the combinations described herein.

It should be understood that one or more of the specific additives described herein can exhibit additional properties and consequently may be categorized in one or more of the classes described herein.

The reagents described herein are prepared and incorporated into any of a wide variety of electrochemical sensors, such as test strips, using conventional methods, including as is described in U.S. Pat. Application Publication 2005/0016844, the disclosure of which is incorporated herein by reference in its entirety.

In another embodiment, electrochemical sensors for detecting and/or measuring glucose in a sample are described. The electrochemical sensors include a reagent composition described herein.

Additional illustrative components that are optionally included in the reagent compositions described herein are described in U.S. Pat. No. 5,122,244, the disclosure of which is incorporated herein by reference.

In another embodiment, the reagent compositions described herein are included in an electrochemical sensor. Illustrative electrochemical sensors are in the form of disposable test strips, such as test strips described in U.S. Pat. Nos. 7,276,146, and 7,276,147, U.S. Pat. Application Publication Nos. US 2005/0016844, US 2005/0013731, and 2005/0019212, the disclosures of which are incorporated herein by reference.

In another embodiment, the reagent compositions described herein are included in an electrochemical sensor. Illustrative electrochemical sensors include a sample-receiving chamber for a fluid sample, and a reagent composition described herein for producing an electrochemical signal in the presence of glucose. In one variation, the sensor comprises a disposable test strip, such as a test strip having a laminar construction providing an edge opening which communicates with the sample-receiving chamber. The reagent is disposed within the sample-receiving chamber in position to provide the electrochemical signal to a working electrode also positioned within the chamber.

In another embodiment, the reagent compositions described herein are included in a sensor that is used in combination with a meter for detecting and/or measuring the glucose in the sample fluid. In one aspect, the meter includes a connection with the electrodes of the sensor and circuitry to evaluate the electrochemical signal corresponding to the presence and/or concentration of the glucose. In optional variations, the meter may also include means for determining that the sample fluid has been received by the sensor, and/or that the amount of sample fluid is sufficient for testing. In another aspect, the meter may store and display the results of the analysis, or may alternatively provide the data to a separate device.

As used herein, the term "electrochemical sensor" generally refers to a device configured to detect the presence of, and/or measure the concentration of, an analyte by way of electrochemical oxidation and reduction reactions within the sensor. These reactions are transduced to an electrical signal that can be correlated to the presence of, and/or an amount or concentration of the analyte.

The electrochemical sensor can be in the form of a test strip. The test strip includes an electrode system comprising a set of measuring electrodes, e.g., at least a working electrode and a counter electrode, within a sample-receiving chamber. The sample-receiving chamber is configured such that sample fluid entering the chamber is placed in electrolytic contact with both the working electrode and the counter electrode. This allows electrical current to flow between the measuring electrodes to affect the electrooxidation or electroreduction of the analyte.

As used herein, a "working electrode" is generally an electrode at which analyte is electrooxidized or electroreduced with or without the agency of a redox mediator. The term "counter electrode" refers generally to an electrode that is paired with the working electrode and through which passes an electrochemical current equal in magnitude and opposite in sign to the current passed through the working electrode. The term "counter electrode" is generally meant to include counter electrodes which also function as reference electrodes (i.e., counter/reference electrodes).

The working and counter electrodes, and the remaining portions of the electrode system, may be formed from a variety of materials, as known in the art. The electrodes should have a relatively low electrical resistance and should be electrochemically inert over the operating range of the test strip. Suitable conductors for the working electrode include gold, palladium, platinum, carbon, titanium, ruthenium dioxide, and indium tin oxide, and iridium, as well as others. The counter electrode may be made of the same or different materials, e.g., silver/silver chloride. In an illustrative embodiment, the working and counter electrodes are both gold electrodes.

The electrodes may be applied to the base substrate in any fashion that yields electrodes of adequate conductivity and integrity. Exemplary processes are well known in the art, and include, for example, sputtering, printing, etc. In an illustrative embodiment, gold electrodes are provided by coating the base substrate and then removing selected portions of the coating to yield the electrode system. An illustrative removal method is laser ablation, including broad field laser ablation, as disclosed in U.S. Pat. No. 7,073,246, entitled Method of Making a Biosensor, the disclosure of which is hereby incorporated by reference.

The electrode system may have a variety of configurations suited to the operation of the test strip and meter. For any embodiment, the working and counter electrodes may be positioned and dimensioned to minimize the volume of sample fluid required to cover them. It is also preferable that the electrodes be configured to maintain a current flux of sufficient magnitude as to be measurable using a relatively inexpensive hand-held meter.

By way of further example, an illustrative embodiment includes a counter electrode which extends around both sides of the working electrode. The counter electrode therefore has two elements, one in front of the working electrode and the other behind the working electrode, as the sample fluid enters the sample-receiving chamber. More specifically, the counter electrode includes two elements which extend across the sample-receiving chamber. Each of these elements is about 250 µm wide. The working electrode element has a width of about 250 µm, and is spaced from each of the two counter electrode elements by about 255 µm. It will be appreciated that this is only one of a number of configurations for the measuring electrodes.

In another embodiment, the electrochemical sensor includes traces and contacts as part of the electrode system. The traces and the contact pads may be provided in a variety of fashions consistent with their intended function relative to the test strip. These components of the electrode system may be composed of the same material as the electrodes, and may be applied to the base substrate in the same manner and simultaneously with the application of the electrodes. In an illustrative embodiment, the traces and contact pads are gold, and are formed by laser ablation, particularly as described in U.S. Pat. No. 7,073,246, which is herein incorporated by reference. However, alternate materials and methods of application may be employed.

In another embodiment, the reagent compositions described herein are included in a test strip. In one aspect, the test strip includes several basic components, including but not limited to, a small body defining a chamber in which the sample fluid is received for testing. The sample-receiving chamber may be filled with the sample fluid by suitable means, such as by capillary action, but also optionally assisted by pressure or vacuum. In another aspect, the sample-receiving chamber includes electrodes and a reagent composition described herein suitable for producing an electrochemical signal indicative of the glucose in the sample fluid.

The test strip includes a chemical reagent within the sample-receiving chamber for reacting with the test analyte to produce the electrochemical signal that represents the presence of the analyte in the sample fluid. The reagent composition can include a variety of active components selected to determine the presence and/or concentration of various analytes. The test chemistry is therefore selected in respect to the analyte to be assessed. As is well known in the art, there are numerous chemistries available for use with each of various analytes. For example, in one preferred embodiment, the test strip of the present invention can include one or more enzymes, co-enzymes, and co-factors, which can be selected to determine the presence of glucose in blood. The selection of an appropriate chemistry is therefore well within the skill in the art, and further description herein is not required in order to enable one to make and use the test strips with various analytes.

In another embodiment, the test strip is a relatively small device that is dimensioned for compactness and ease of storage and use. Illustratively, the strip length is in the range of about 20 to about 50 mm, about 33 to about 38 mm, in length, and about 5 to about 15 mm, or about 7 to about 9 mm, in width. In another aspect, the test strip includes a slot or vent opening to the edge of the meter, which may be sized to provide a grab area where there is no sample fluid present, and/or to decrease or prevent the presence of blood contamination of the meter contact area. Illustrative dimensions of the slot or vent opening may be in the range of about 5 to about 35 mm, or at least about 13 mm. The total length of the test strip portion is illustratively about 6.0 mm or less, along the long axis of the test strip.

In another aspect, the test strip is of a laminar construction and is relatively thin illustratively, the overall thickness of the test strip may be about 500 to about 525 µm. In another aspect, the thickness of the test strip portion that is inserted into the meter contact is less than the overall thickness, such as about 250 µm.

In another embodiment, the reagent layer has a thickness of between about 1 and 20 microns. In another embodiment, the reagent layer has a thickness of between about 2 and 6 microns. In another embodiment, the chamber has a height from about 50 µm to about 200 µm. In another embodiment, the chamber has a height from about 120 µm to about 180 µm. In another embodiment, the chamber has a volume of less than 1.0 µL. In another embodiment, the chamber has a volume of less than 0.5 µL. In another embodiment, the chamber has a volume from about 0.15 µL to about 1.4 µL. In another embodiment, the chamber has a volume from about 0.4 µL to about 0.7 µL.

In another embodiment, the test strip includes a base substrate that comprises an insulating material supporting the electrode system and other components. Illustrative base substrates include plastics such as vinyl polymers, polyimides, polyesters, and styrenes that may provide desirable electrical and structural properties. Illustrative base substrates include plastics such as a flexible polymeric material including, but not limited to, polyester, such as high temperature polyester materials; polyethylene naphthalate (PEN), and polyimide, or mixtures of two or more of the foregoing. Suitable polyimides are available commercially, for example under the trade name KAPTON, MELINEX 329, from E.I. duPont de Nemours and Company of Wilmington, Del. (duPont), and the like.

The reagent composition can be deposited on the test strip surface using a variety of conventional coating methods including curtain coating, hot melt coating, rotary screen coating, doctor blade or air knife coating, Meyer bar coating, and reverse roll coating techniques. Illustratively, the reagent composition is applied to the web by a slot-die coating process. The reagent composition may be deposited on the flexible web as a wet composition at a thickness of between about 40 µm and about 100 µm. Alternatively, the reagent composition may deposited as a wet composition at a thickness of between about 60 µm and about 80 µm. The composition may be applied as a uniformly thin layer of a reagent directly on top of the measuring electrodes and along the length of a web of multiple test strips, as a continuous narrow band. In another embodiment, the narrow band has a width of between about 7 mm and 8 mm and a dry thickness of between about 3 µm and about 20 µm. The composition may also be applied onto other electrodes that may reside in the sample-receiving chamber, depending on the desired functionality of such extraneous electrodes. In another embodiment, test strips are fabricated using reel-to-reel process.

In another embodiment, test strips are described having a small sample-receiving chamber less than 1 microliter, or less than 0.5 microliter. The sample-receiving chamber includes a uniform reagent layer that avoids undesirable edge and meniscus effects.

In another embodiment, test strips are described having meter insertion and sample-receiving ends, first and second sides, and a central longitudinal axis that is oriented substantially parallel to the two sides. In another embodiment, the test strip defines a downstream direction from the sample-receiving end to the meter insertion end. In another embodiment, the test strip includes a base substrate having an electrode formed thereon. A spacing layer overlies the base substrate and has a void or cavity that at least partially defines the sample-receiving chamber. In another embodiment, the reagent layer is disposed in the sample-receiving chamber and covers a portion of the base substrate and the electrode. In another embodiment, the reagent layer is sandwiched between the spacing layer and the base substrate and extends to the first and second sides of the base substrate and also extends to the sample-receiving end of the test strip.

In another embodiment, the sample-receiving chamber defines a channel aligned with the longitudinal axis and has a sample-receiving opening disposed at the sample-receiving end. In another embodiment, the reagent layer extends to the sample-receiving opening. It is appreciated that this arrangement may ensure that an even and smooth reagent layer coats most or all of the floor of the sample-receiving chamber, thereby avoiding edge discontinuities, meniscus effects and other inhomogeneities in the reagent layer.

In another embodiment, the test strip includes a covering layer overlying the spacing layer. Illustratively, the covering layer includes a vent opening that communicates with the sample-receiving chamber, thereby allowing air to escape the chamber as fluid enters it. In another embodiment, the reagent layer extends in the downstream direction all the way to the vent opening, if not slightly beyond it. It is appreciated that as the sample fluid is drawn into the sample-receiving chamber by capillary action, it experiences a uniform and thin reagent layer until it stops at the vent opening, which is provided as a slot with one side thereof being hydrophobic, thereby effectively halting movement of the sample beyond it.

In another embodiment, the electrodes on the base substrate include a working electrode and a counter electrode, both of which are covered by the reagent layer. Illustratively the reagent layer extends in the downstream direction beyond the electrodes.

In another embodiment, the reagent layer defines first and second reagent layer side edges that are substantially aligned with the first and second sides of the test strip. Illustratively, the reagent layer also forms a reagent layer end edge that is aligned with the sample-receiving end of the test strip. In another embodiment, the reagent layer edges are formed as part of the die cutting process that forms individual test strips from a larger web, providing a smooth and even edge that avoids undesirable edge effects.

In another embodiment, the test strip includes an adhesive layer sandwiched between the spacing layer and the base substrate. Illustratively, the adhesive layer is formed having an edge profile that is aligned with the peripheral edge of the sample-receiving chamber. In another embodiment, the adhesive forms a seal around the periphery of the sample-receiving chamber, thereby preventing sample fluid from wicking laterally outside of the chamber and spreading under the spacing layer.

In another embodiment, the reagent layer can not only be made very thin but also show a high homogeneity down and across the web in the reaction area. Illustratively, the reagent layer in the test area or sample receiving chamber is flat and uniform in thickness. It is to be understood that thickness variations in the coated stripe may occur, but are illustratively limited to the outer 0.2 cm (or less) edges of the stripe.

In another embodiment, the test strip includes a covering layer having a slot. Illustratively, the slot divides the covering layer into two parts and provides a vent opening that allows air to escape a cavity or sample receiving chamber formed in the test strip as fluid enters it. In another embodiment, the covering layer is clear, such that the user can see through it and the slot doubles as a fill line. The user can thus watch the fluid sample enter the test strip, progress through the capillary cavity, and then stop at the slot or fill-line. This provides positive assurance to the user that the sample size is sufficient and the test strip has been filled properly.

In another embodiment, the test strip includes a sample receiving chamber having a flared portion that terminates in a sample receiving opening. Illustratively, the flared portion provides a reservoir from which sample fluid can be drawn into the capillary or sample receiving chamber, aids the user in introducing the sample to the test device, and reduces dose hesitation. In another embodiment, the hydrophilic reagent layer extends to the dosing end or side of the test strip and further promotes wicking of the sample into the sample receiving chamber and thus further reduces dose hesitation.

The reagent compositions described herein may be illustratively applied to a surface of the test strip using a process described in U.S. Pat. No. 7,749,437, the disclosure of which is incorporated herein by reference.

In another embodiment, the reagent compositions described herein may be included in or on an electrochemical sensor for detecting and/or measuring glucose in a sample. Illustratively, the sample may be an aqueous sample, a blood sample, and the like. Illustratively, the electrochemical sensor includes an electrode, such as, but not limited to, an electrode described in U.S. Pat. Nos. 6,662,439 and 7,073,246, the disclosures of which are incorporated herein by reference.

In another embodiment, the reagent compositions described herein may be included in or on, or be used in conjunction with a device for detecting and/or measuring glucose in a sample. Illustratively, the sample may be an aqueous sample, a blood sample, and the like. Illustratively, the device may include algorithms and methods for processing a signal generated either directly or indirectly by the reagent composition, such as, but not limited to, methods and algorithms described in U.S. Pat. Nos. 6,645,368, 7,407, 811, 7,488,601, 7,452,457, 7,597,793, 7,494,816, and 7,569, 126, the disclosures of which are incorporated herein by reference.

In another embodiment, methods for detecting and/or measuring glucose in a sample are described. The methods include the step of contacting a sample containing glucose with a reagent composition described herein. It is to be understood that the reagent composition may be configured in any of a variety of formats, including formats described herein such as a dried reagent layer on a test strip. In another embodiment, the reagent compositions described herein are included in a system that is useful for assessing glucose in a sample fluid. The system includes devices and methods for evaluating the sample fluid for glucose. As more fully described hereafter, the evaluation may range from detecting the presence of glucose to determining the concentration of glucose. In another embodiment, the sample is a biological fluid, such as blood or interstitial fluid.

Referring to the test sample, illustratively, the majority of the chamber is hollow before use. In the very small sample chamber of the test strips described herein, the reagent layer is illustratively thin and uniform. Because the sample-receiving chamber is very small, less than about 1 μl, the depth or vertical height of the chamber is also small. Consequently, the reagent layer may not occupy the majority of the internal cavity of the chamber. The reagent layer may be sufficiently thin to leave ample space for the test sample in the chamber. Further, the liquid test sample will hydrate or dissolve the thin reagent layer more quickly. Illustratively, the mediator, or mediator precursor, and mediator redox products diffuse through and within the reagent layer/gradient to the electrodes. The reactive components and intermediates will have a short distance to diffuse through a thin reagent, therefore, diffusion to the electrodes will occur in less time. Additionally, the capture efficiency of mediator redox products at an electrode will be greater for a thin layer of enzyme than a thick layer. Conversely, a thick reagent layer will take more time for the liquid test sample to hydrate or dissolve, and a thick reagent layer will increase the time that it takes for the mediator/mediator redox products to approach the electrodes. This increased time may delay the time to determine the analyte concentration and introduce errors into the determination.

It is appreciated herein that thickness inhomogeneity can lead to variability in determining the analyte concentration. In another embodiment, the reagent layer has a uniform thickness throughout the entire sample receiving chamber. Illustratively, the reagent layer is not thicker around the perimeter of the sample receiving chamber adjacent the vertical side walls that define the chamber than in the central portion of the chamber. Consequently, the reagent layer does not exhibit a meniscus profile.

In another embodiment, the reagent composition is formulated as a viscous solution that can be deposited in a thin, uniform layer on the base layer. Illustratively, the reagent composition includes thickeners and thixotropic agents to enhance the physical properties of the reagent layer. The thickeners are selected to provide a thick, liquid matrix having the remaining components homogeneously dispersed therein. The thickening and thixotropic agents also inhibit the liquid or semi-paste material from running or spreading over the surface of the base layer after it has been deposited and before it dries. After the reagent composition is deposited, it quickly dries to a readily hydratable matrix.

The reagent composition advantageously dries rapidly either with air drying or heat drying. After drying, the deposited reagent layer illustratively exhibits a thickness of between about 1 micron and about 20 microns. In another embodiment, the dried reagent layer exhibits a thickness of between about 2 microns and about 6 microns.

EXAMPLES

Preparation of Reagent Compositions. The components of the reagent composition are illustratively admixed with water to provide a homogeneous, viscous suspension. The order of addition is not essential. A sufficient amount of the buffer solution is added to maintain the reagent composition at a desired pH, such as a pH of about 7. Illustratively, the selected components are pre-mixed with water to provide a variety of stock solutions that can be combined to yield the final reagent composition. For example, a buffer solution can be prepared by combining the phosphate salts and, optionally, the sodium succinate. Other stock solutions include: the thickening agents, i.e., Keltrol F and the carboxymethyl cellulose; the surfactants, i.e., Geropon T77 and Mega 8; the enzyme and coenzyme or cofactor; and the mediator.

Referring to FIG. 1, the kinetic performance of a PQQ-GDH enzyme used in the reagent when PIPES, β-glycerophosphate, and phosphate are the buffers is shown. Test strips fabricated using reagent compositions described herein are dosed with an aqueous control solution containing approximately 500 mg/dL glucose. A potential of 450 mV is applied to the strip electrodes. As shown in FIG. 1, the DC response is monitored over time. In particular, the time required for the response to reach a maximum is recorded for each test strip. The time required for the DC response to reach a maximum is indicative of the kinetics of the enzymatic glucose reaction. When the time required for the DC response to reach its maximum is short, the kinetics can be described as fast. Conversely, when the time required for the DC response to reach its maximum is long, the kinetics can be described as slow. As can be seen in FIG. 1, referring specifically to trace A, the test strip using a PIPES based-reagent reaches the DC peak maxim at approximately 2300 ms. Referring now to trace B and C, the test strips using either a phosphate buffer based-reagent or a β-glycerophosphate buffer based reagent reaches the DC peak maxima at approximately 4000 ms.

Accelerated stability studies are performed to evaluate the difference in stability between a PQQ-GDH enzyme combined with an exemplary PIPES buffer and a PQQ-GDH enzyme combined with a comparative phosphate buffer. Test strips fabricated with the exemplary and comparative reagent compositions described herein are stored for four weeks, one set being stored at 4° C. and the other set at 45° C. The strips are then tested using linearity solutions with target glucose levels of 45 mg/dL (LIN 2), 307 mg/dL (LIN 4), and 559 mg/dL (LIN 6). The mean DC response of the strips held at 45° C. is determined for each glucose level, and this response is then compared to the DC response of the strips held at 4° C. The results from this testing are shown in Table 1 below. Test strips containing a reagent including a PIPES buffer show enhanced stability compared to both the reagent including the β-glycerophosphate buffer and the reagent including the phosphate buffer. Specifically, for low glucose levels (45 mg/dL, LIN 2), the bias difference between the strips stored at 4° C. and the strips stored at 45° C. was 12% lower than the strips with the β-glycerophosphate buffer reagent and 18% lower than strips with the phosphate buffer reagent. For mid glucose levels (307 mg/dL, LIN 4), the bias difference between the strips stored at 4° C. and the strips stored at 45° C. was 8% lower than the strips with the β-glycerophosphate buffer reagent and 23% lower than strips with the phosphate buffer reagent. For high glucose levels (559 mg/dL, LIN 6), the bias difference between the strips stored at 4° C. and the strips stored at 45° C. was 7% lower than the strips with the β-glycerophosphate buffer reagent and 21% lower than strips with the phosphate buffer reagent. These data indicate that PIPES buffer helps to stabilize the enzyme, enabling it to be less susceptible to degradation over long periods of time at high temperatures.

TABLE 1

Stability Response of PQQ-GDH Enzyme Strips Containing Various Buffers

| Buffer | Target Glucose (mg/dL) | Temperature | Time Point (weeks) | Mean % Bias to 4° C. |
|---|---|---|---|---|
| PIPES | 45 | 45° C. | 4 | −3.39 |
|  | 307 | 45° C. | 4 | −10.81 |
|  | 559 | 45° C. | 4 | −9.74 |
| Phosphate | 45 | 45° C. | 4 | −21.47 |
|  | 307 | 45° C. | 4 | −33.53 |
|  | 559 | 45° C. | 4 | −30.83 |
| β-glycerophosphate | 45 | 45° C. | 4 | −15.72 |
|  | 307 | 45° C. | 4 | −18.64 |
|  | 559 | 45° C. | 4 | −16.26 |

Without being bound by theory, it is believed herein that the DC response directly influences the strip performance, where smaller biases are indicative of more precise and accurate test strips. Table 1 shows the DC bias that results from test strips having the comparative and exemplary reagents being stressed at 45° C. for four weeks compared to the DC of strips that have been stored at 4° C. for four weeks. The greater the DC response degrades, the more negative bias that is observed with the background response. The negative bias in DC terms is usually associated with enzyme degradation. Table 1 shows that the reagent that contains PIPES buffer shows a less negative DC bias, indicating that the enzyme is more stable when held at this elevated temperature for lengthy periods of time in the presence of reagent compositions described herein. The biases observed with phosphate buffer and β-glycerophosphate buffer are more negative, indicating the enzyme is less stable in those buffers. The values in Table 1 may also be expressed as bias difference (12%, 8%, and 6.5%) corresponding to the bias improvements that zwitterionic buffers, such as PIPES, yield over that of β-glycerophosphate. For example, at 45 mg/dL glucose, the DC bias with PIPES is −3.39%, while the bias is −15.72% with β-glycerophosphate. This is a difference of ~12%. At 307 mg/dL, the bias is −10.81% vs. −18.64%, for a difference of ~8%, etc. Similar performance improvements were observed with test strips containing FAD-GDH and zwitterionic buffers, such as PIPES, compared to non-zwitterionic buffers.

Table 2 shows data that mirrors that collected and set forth in Table 1, except test strips including MOPS buffer are compared with test strips including β-glycerophosphate (B-GPO4) buffers at two different pH values. The observations made herein regarding the stability of the enzyme included in the test strip with the PIPES buffer are qualitatively the same as those seen for the test strips including the MOPS buffer. That observation indicates that the enzyme is more stable in the test strips that include a MOPS buffer. To assess the impact of the different pH values of the conventional β-glycerophosphate buffer and the MOPS buffer, a set of test strips were made using a β-glycerophosphate buffer at pH=7.5 and run concurrently with the MOPS and a β-glycerophosphate buffer at pH=7.0.

TABLE 2

Stability Response of PQQ-GDH Enzyme Strips Containing Various Buffers

| Buffer | Target Glucose (mg/dL) | Temperature | Time Point (weeks) | Mean % Bias to 4° C. |
|---|---|---|---|---|
| pH = 7.0 B-GPO4 | 45 | 45° C. | 4 | −11.01 |
|  | 307 | 45° C. | 4 | −13.75 |
|  | 559 | 45° C. | 4 | −14.16 |
| pH = 7.5 B-GPO4 | 45 | 45° C. | 4 | −9.46 |
|  | 307 | 45° C. | 4 | −13.95 |
|  | 559 | 45° C. | 4 | −14.36 |
| pH = 7.5 MOPS | 45 | 45° C. | 4 | 3.26 |
|  | 307 | 45° C. | 4 | −2.81 |
|  | 559 | 45° C. | 4 | −3.15 |

Figure 2:
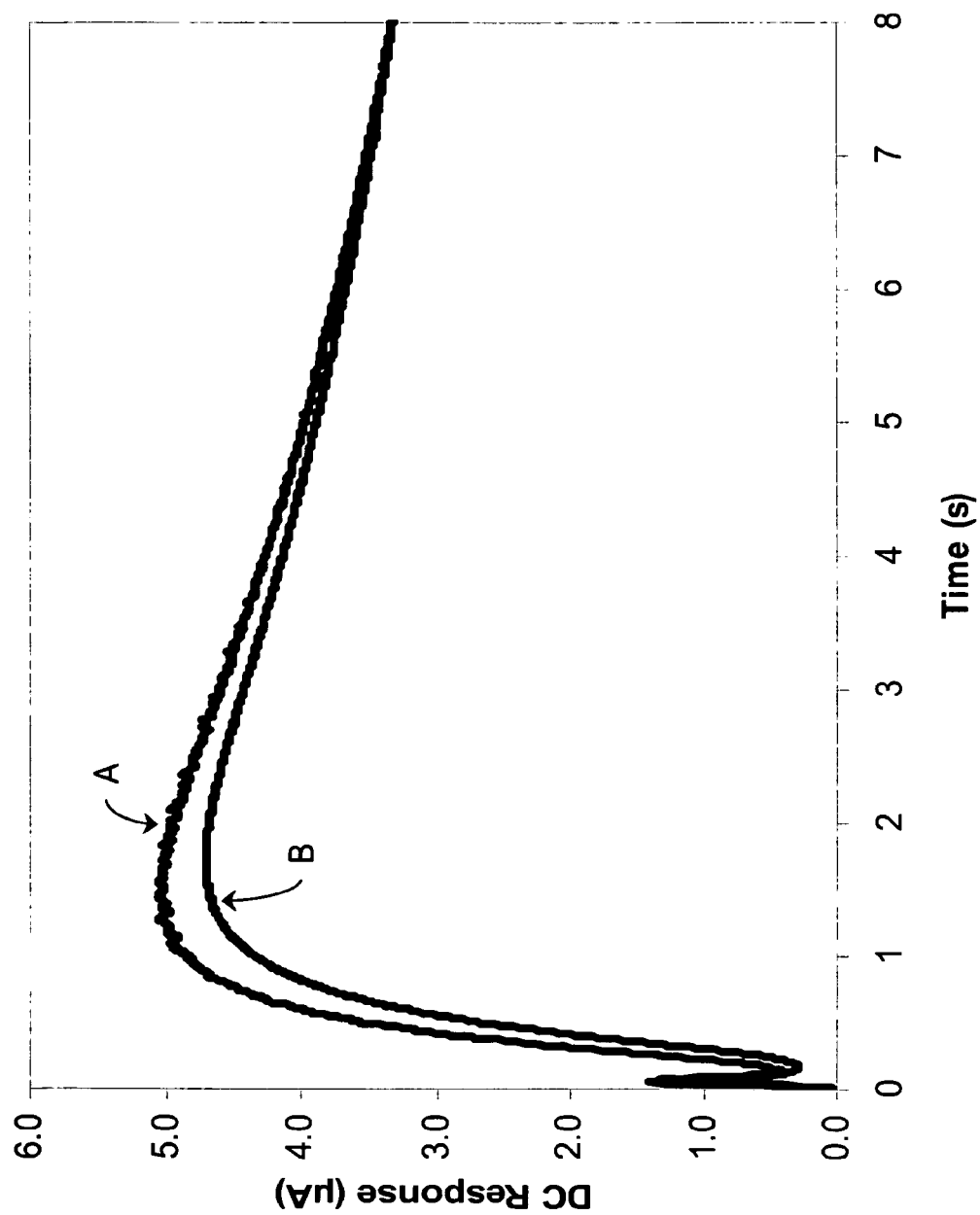
FIG. 2 shows the kinetics curves for DC response (μA) versus time (ms) for two illustrative sensors based on a FAD-GDH enzyme using reagents that include (A) a PIPES buffer, and (B) a phosphate buffer.
Figure 3:
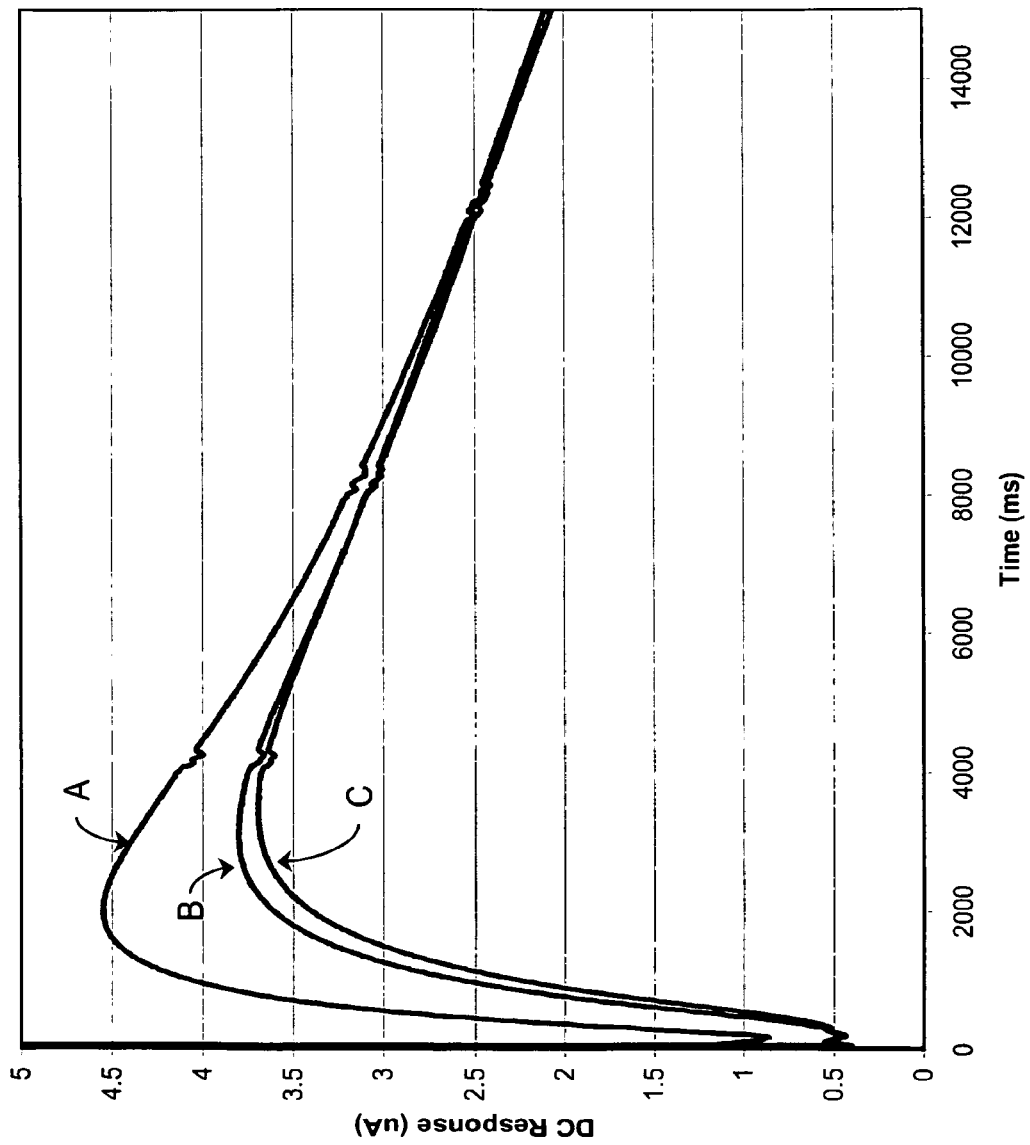
FIG. 3 shows the kinetics curves for DC response (μA) versus time (ms) for three illustrative sensors using reagents that include (A) a MOPS buffer at a pH of 7.5, (B) a β-glycerophosphate buffer at a pH of 7.5, and (C) a β-glycerophosphate buffer at a pH of 7.0.

Referring to FIG. 2, trace A and trace B show the kinetic performance of two exemplary reagents using the FAD-GDH enzyme in a test strip with reagent compositions as described herein. FIG. 2 shows the kinetics curves for DC response (µA) versus time (ms) for two equivalent sensors based on FAD-GDH using reagents that include a PIPES buffer (A) and a phosphate buffer (B). Similarly, FIG. 3 shows the kinetics curves for DC response (µA) versus time (ms) for three equivalent sensors using reagents that include a MOPS buffer at a pH of 7.5 (A), a β-glycerophosphate buffer at a pH of 7.5 (B), and a β-glycerophosphate buffer at a pH of 7.0. As is described herein for FIG. 1 with respect to the PQQ-GDH enzyme, the strips used to generate FIGS.

2 and 3 are dosed with a control solution containing approximately 500 mg/dL glucose and the DC current response is monitored over time. For strips with PIPES buffer, the DC current reaches a maximum value in 1.43 seconds, compared to 1.72 seconds for strips with phosphate as the buffer, as shown in FIG. 2. The decrease in time to maximum current indicates that the enzyme reaction with glucose is enhanced and/or preserved by the use of zwitterionic buffers, such as PIPES buffer and/or MOPS buffer, as shown in FIG. 3.

Figure 4:
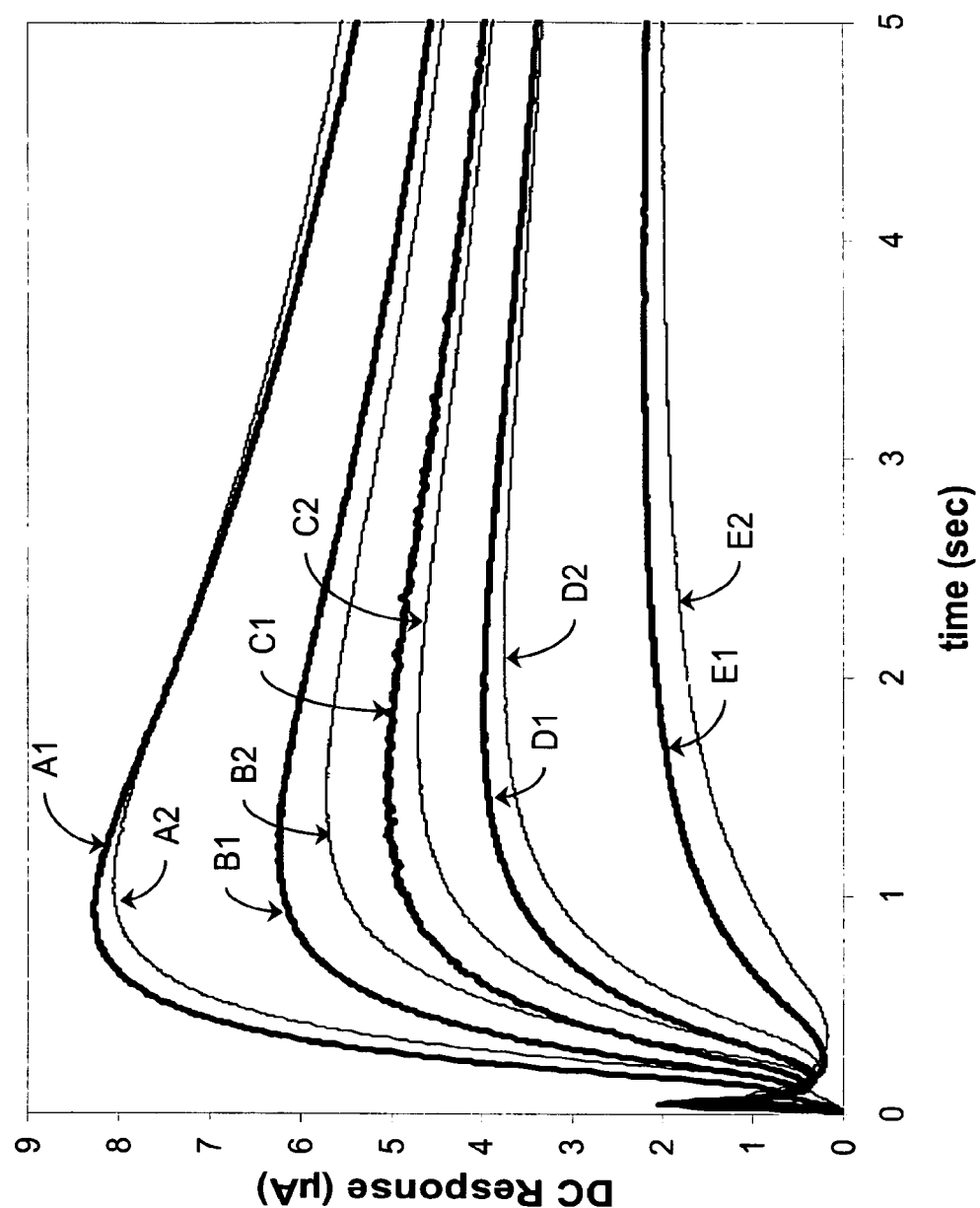
FIG. 4 shows the kinetics curves for DC response (μA) versus time (ms) to ~500 mg/dl glucose in an aqueous sample for ten illustrative sensors based on FAD-GDH using reagents that include (A1) a PIPES buffer operating at 42° C., (A2) a phosphate buffer operating at 42° C., (B1) a PIPES buffer operating at 30° C., (B2) a phosphate buffer operating at 30° C., (C1) a PIPES buffer operating at 24° C., (C2 a phosphate buffer operating at 24° C., (D1) a PIPES buffer operating at 12° C., (D2 a phosphate buffer operating at 12° C., (E1) a PIPES buffer operating at 6° C., (E2) a phosphate buffer operating at 6° C.
Figure 5:
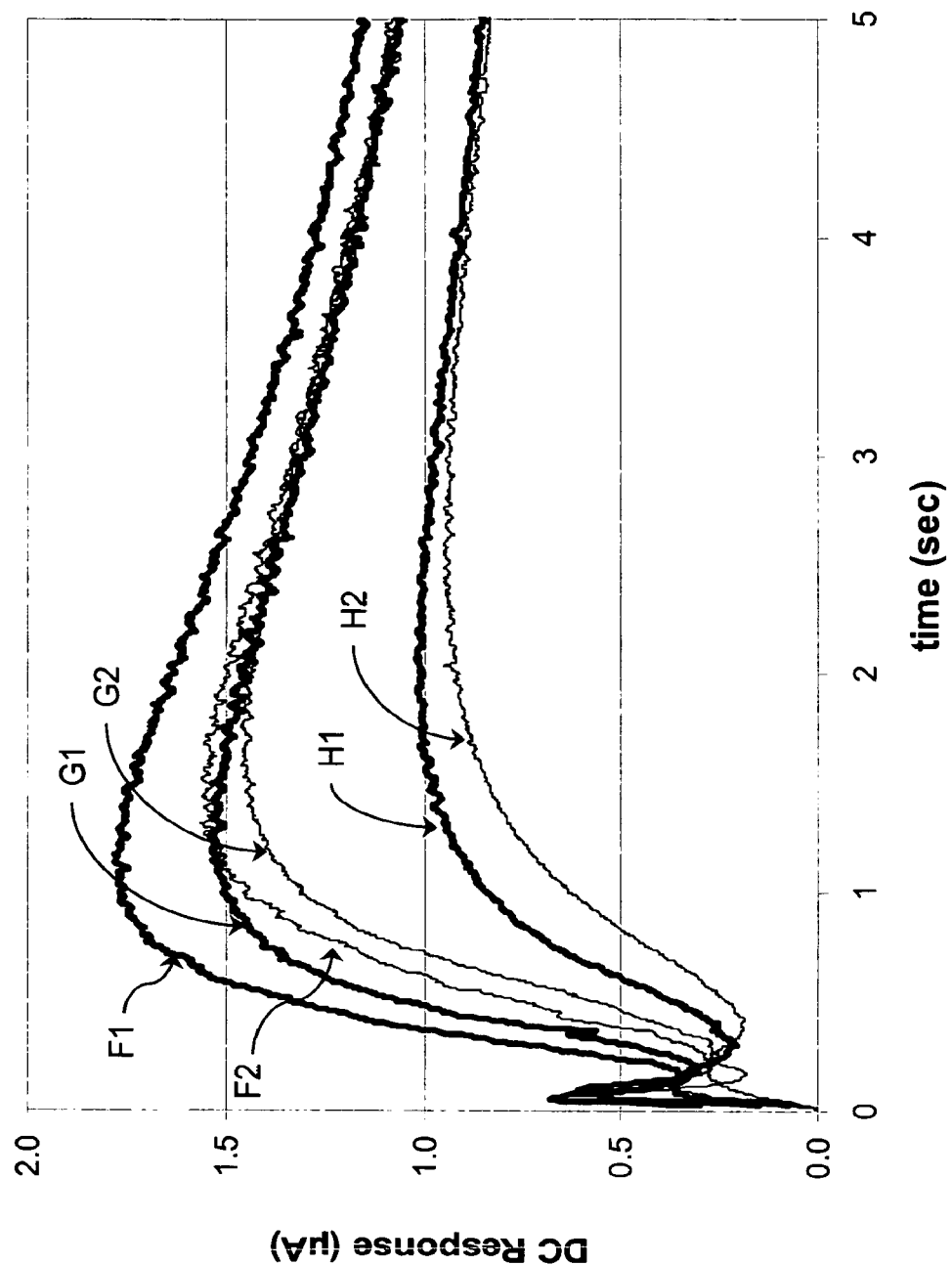
FIG. 5 shows the kinetics curves for DC response (μA) versus time (ms) to ~200 mg/dl glucose in a stabilized human blood sample for six illustrative sensors based on FAD-GDH using reagents that include (F1) a PIPES buffer operating at 24° C., (F2) a phosphate buffer operating at 24° C., (G1) a PIPES buffer operating at 18° C., (G2) a phosphate buffer operating at 18° C., (H1) a PIPES buffer operating at 6° C., (H2) a phosphate buffer operating at 6° C.

Referring to FIG. 4, kinetic curves for the response to glucose of test strips having FAD-GDH enzyme comparing strips including PIPES buffer and phosphate buffer are shown. Specifically, FIG. 4 shows the kinetics curves for DC response (μA) versus time (ms) for ten otherwise equivalent sensors based on FAD-GDH using reagents that include a PIPES buffer operating at 42° C. (A1), a phosphate buffer operating at 42° C. (A2), a PIPES buffer operating at 30° C. (B1), a phosphate buffer operating at 30° C. (B2), a PIPES buffer operating at 24° C. (C1), a phosphate buffer operating at 24° C. (C2), a PIPES buffer operating at 12° C. (D1), a phosphate buffer operating at 12° C. (D2), a PIPES buffer operating at 6° C. (E1), and a phosphate buffer operating at 6° C. (E2) showing a response to ~500 mg/dL glucose in an aqueous sample. Strips including a PIPES buffer show enhanced reaction kinetics at low and high temperature compared to strips with phosphate buffer. The increase in reaction kinetics is observed using both an aqueous control solution with glucose concentration of approximately 500 mg/dL (FIG. 4) and a stabilized human blood control solution with glucose concentration of approximately 200 mg/dL (FIG. 5). Without being bound by theory, it is believed herein that by enabling the DC response to stabilize more quickly at low temperatures, the precision and temperature range of test strips that include a reagent including a zwitterionic buffer, such as PIPES buffer, and FAD-GDH is enhanced.

Referring to FIG. 5, shown are the kinetics curves for DC response (μA) versus time (ms) for six otherwise equivalent sensors based on FAD-GDH using reagents that include a PIPES buffer operating at 24° C. (F1), a phosphate buffer operating at 24° C. (F2), a PIPES buffer operating at 18° C. (G1), a phosphate buffer operating at 18° C. (G2), a PIPES buffer operating at 6° C. (H1), and a phosphate buffer operating at 6° C. (H2) showing a response to ~200 mg/dL glucose in a stabilized human blood sample. As is shown with FIG. 4, an increase in reaction kinetics is observed. Without being bound by theory, it is believed herein that enabling the DC response to stabilize more quickly at low temperatures, the precision and temperature range of test strips that include a reagent including a zwitterionic buffer, such as PIPES buffer, and FAD-GDH is enhanced.

Figure 6:
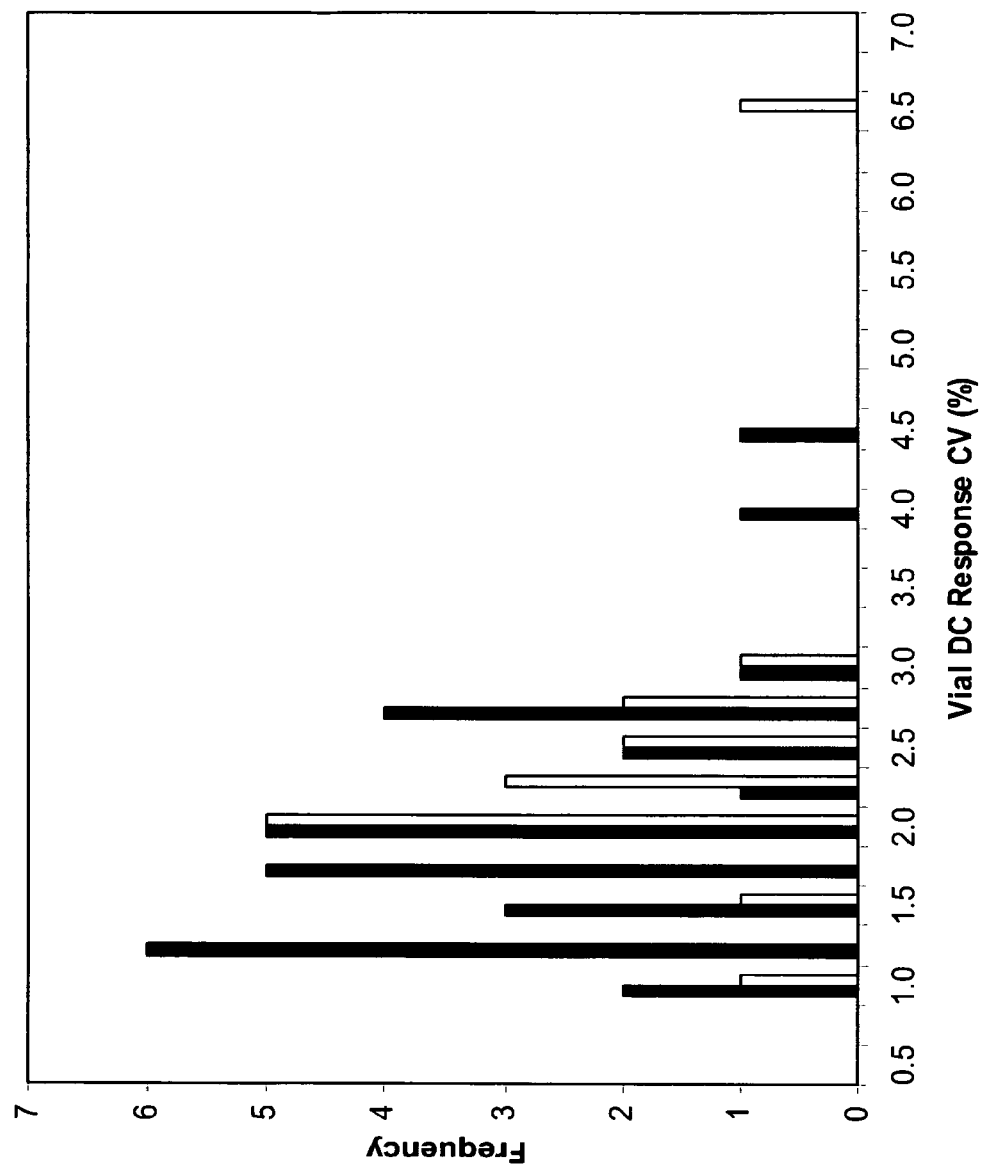
FIG. 6 shows a comparison of vial DC response CV for illustrative sensors including a PIPES buffer (solid bars), and a phosphate buffer (open bars).

FIG. 6 shows a histogram of vial DC response CV. A comparison of the precision of test strips including a zwitterionic buffer (solid bars) and a phosphate buffer (open bars) is shown. The data indicate that the precision of the DC response is improved when using a PIPES buffer compared to a phosphate buffer. Vials are sampled regularly across a coated roll and eight strips per vial are tested with a control solution containing approximately 500 mg/dL glucose in an aqueous matrix. The histogram shows the number of vials (frequency) on the y-axis that have a given DC response coefficient of variation (CV) range shown on the x-axis. The DC response CV is the coefficient of variation of DC response across the eight of test strips in a vial. Test strips are made according to procedures described herein, and using conventional processes, except that one population of vials is made using a phosphate buffer and one population of vials is made using a PIPES buffer. The CV of the DC response for each vial is calculated. The median vial DC Response CV for the test strips using a PIPES buffer was 1.7%, while the test strips using a phosphate buffer had a median of 2.1%. The spread in CV values was also reduced by using PIPES buffer, with the maximum CV/minimum CV values 4.2%/0.79% and 6.3%/0.82% for test strips using a PIPES buffer and test strips using a phosphate buffer, respectively.

FIG. 7 shows high glucose stability response of FAD-GDH strips containing PIPES (squares) and phosphate buffer (diamonds). Test strips are prepared using an exemplary PIPES buffer and other test strips are prepared using a comparative phosphate buffer, both using FAD-GDH enzyme. Briefly, test strips using the PIPES buffer show better enzyme stability at elevated temperatures. The enzyme stability of test strips including FAD-GDH enzyme was evaluated under high temperatures for extended periods of time in closed vials. High glucose control solutions with FAD-GDH may be used to evaluate enzyme stability because there is no inhibition of the enzyme by glucose at high levels. The mediator stability is acceptable under these conditions; therefore, it is believed that the decrease in DC response is due to a decrease in enzyme activity caused by thermal degradation of the FAD-GDH. The bias of the DC response is monitored when test strips are dosed with a high glucose control solution at 45° C. vs. 4° C. The test strips prepared using phosphate buffer are able to maintain the high glucose DC response when stored at 45° C. for up to 16 weeks; however, after 16 weeks at 45° C., the response decreased significantly. Test strips prepared with zwitterionic buffer, such as PIPES buffer are able to maintain the high glucose dose response with little decrease upon storage at 45° C. for the duration of the study, indicating that the inclusion of PIPES buffer stabilized the FAD-GDH in the reagent composition.

Though illustrative and exemplary embodiments incorporating the principles of the present invention have been disclosed hereinabove, it is to be understood that the invention described herein is not limited to the disclosed embodiments. Instead, this application is intended to cover those additional embodiments of the invention that come within known or customary practice in the art to which this invention pertains and which fall within the limits of the claims, or equivalents thereof.

The invention claimed is:

1. An electrochemical sensor comprising an electrode and a dried reagent composition covering at least a portion of the electrode, where the dried reagent composition comprises (a) one or more enzymes selected from the group consisting of glucose dehydrogenases, glucose oxidoreductases, and combinations thereof; (b) one or more mediators, mediator precursors, or a combination thereof, wherein at least one mediator or mediator precursor is aqueous soluble; (c) one or more zwitterionic buffers selected from the group consisting of 2-(N-morpholino)ethanesulfonic acid (MES), piperazine-N,N'-bis(2-ethanesulfonic acid) (PIPES), N-(2-Acetamido)-2-aminoethanesulfonic acid (ACES), (4-(2-hydroxyethyl)-1-piperazineethanesulfonic acid) (HEPES), N-(Tri(hydroxymethyl)methyl)glycine (tricine), N,N-Bis(2-hydroxyethyl)glycine; (bicine), 3-(N-morpholino)propanesulfonic acid (MOPS), N-cyclohexyl-3-aminopropanesulfonic acid (CAPS), N,N-Bis(2-hydroxyethyl)-2-aminoethanesulfonic Acid (BES), N-(Hydroxyethyl)piperazine-N'-2-hydroxypropanesulfonic acid (HEPPSO), and N-(2-Acetamido)iminodiacetic acid (ADA); and (d) one or more thickeners; where the sensor is configured for generating a current response to glucose in an aqueous sample; and where the time from contact with the aqueous sample to the DC maximum current response is about 4 seconds or less.

2. The electrochemical sensor of claim 1 having a time to DC maximum of about 3 seconds or less at ambient temperature.

3. The electrochemical sensor of claim 1 wherein the thickeners comprise one or more gelling agents.

4. The electrochemical sensor of claim 3 comprising a hydroxymethylcellulose, hydroxyethylcellulose, methylhydroxyethylcellulose, or xanthan gum, or a combination thereof.

5. The electrochemical sensor of claim 1 wherein the reagent composition comprises a glucose dehydrogenase (GDH) enzyme, where the GDH is selected from the group consisting of a wild-type GDH, a mutant GDH, and a GDH coenzyme.

6. The electrochemical sensor of claim 1 wherein the enzyme is a mutant GDH exhibiting maltose insensitivity or thermal stability, or both maltose insensitivity and thermal stability.

7. The electrochemical sensor of claim 1 wherein the enzyme is a FAD-GDH or a PQQ-GDH.

8. The electrochemical sensor of claim 1 wherein the zwitterionic buffer is selected from the group consisting of PIPES, MOPS, ACES, and N-(2-acetamido)iminodiacetic acid, or a combination thereof.

9. The electrochemical sensor of claim 1 wherein the zwitterionic buffer is PIPES or MOPS, or a combination thereof.

10. The electrochemical sensor of claim 1 comprising a nitrosoaniline.

11. The electrochemical sensor of claim 1 further comprising one or more adjuvants selected from the group consisting of viscosity adjusting agents, film forming agents, stabilizers, pH adjusting agents, additional buffers, detergents, fillers, film opening agents, coloring agents, thixotropic agents, dispersants, and surfactants, and combinations thereof.

12. The electrochemical sensor of claim 11 comprising a silica, a polyvinyl acetate propionate co-polymer, a polyvinyl propionate, a polyvinylpyrrolidone, a succinate, a trehalose, an acyl-N-methylglucamide, or a fatty acid salt, or any combination thereof.

13. A device for measuring glucose in a sample, the device comprising a base, a spacing layer comprising a void or cavity, and the electrochemical sensor of claim 1, where the spacing layer overlies the base thereby forming a chamber, wherein the electrochemical sensor is included in the chamber.

14. The device of claim 13 wherein the chamber is formed from a base substrate and a covering layer overlying the base substrate; and where the chamber is disposed between the base substrate and the covering layer.

15. The device of claim 13 wherein the chamber includes a flared portion terminating in a fluid receiving opening and an elongated portion extending inwardly from the flared portion.

16. The device of claim 13 further comprising a vent in communication with the chamber, whereby air can escape from the vent when fluid is drawn into the chamber.

17. The device of claim 13 wherein the chamber has a volume of 1.0 µL or less.

18. The device of claim 13 wherein the chamber has a volume of 0.5 µL or less.

19. The electrochemical sensor of claim 1 wherein the (b) one or more mediators, mediator precursors, or a combination thereof, are selected from the group consisting of N,N'-bis-(2-hydroxyethyl)-p-nitrosoaniline, N,N'-dimethyl-p-nitrosoaniline, N,N'-diethyl-p-nitrosoaniline, N-methyl-N'-(4-nitrosophenyl)-piperazine, N-(2-hydroxyethyl)-5-nitrosoindoline, 2,4-dimethoxy-nitrosobenzene, N,N'-bis-(2-methoxyethyl)-4-nitrosoaniline, N-(4-nitrosophenyl)-morpholine, N-(2,2-diethoxy-ethyl)N'-(4-nitrosophenyl)-piperazine, p-nitrosophenol, 3-methoxy-4-nitrosophenol, N-(2-hydroxyethyl)-N'-p-nitrosophenyl-piperazine, N,N-bis-(2-hydroxyethyl)-p-nitrosoaniline, o-methoxy-[N,N-bis-(2-hydroxyethyl)]-p-nitrosoaniline, p-hydroxynitrosobenzene, N-methyl-N'-(4-nitrosophenyl)-piperazine, p-quinone dioxime, N,N-dimethyl-p-nitrosoaniline, N,N-diethyl-p-nitrosoaniline, N-(4-nitrosophenyl)-morpholine, N-benzyl-N-(5'-carboxypentyl)-p-nitrosoaniline, N,N-dimethyl-4-nitroso-1-naphthylamine, N,N,3-trimethyl-4-nitrosoaniline, N-(2-hydroxyethyl)-5-nitrosoindoline, N,N-bis-(2-hydroxyethyl)-3-chloro-4-nitrosoaniline, 2,4-dimethoxy-nitrosobenzene, N,N-bis-(2-methoxyethyl)-4-nitrosoaniline, 3-methoxy-4-nitrosophenol, N-(2-hydroxyethyl)-6-nitroso-1,2,3, tetrahydroquinoline, N,N-dimethyl-3-chloro-4-nitrosoaniline, N,N-bis-(2-hydroxyethyl)-3-fluoro-4-nitrosoaniline, N,N-bis-(2-hydroxyethyl)-3-methylthio-4-nitrosoaniline, N-(2-hydroxyethyl)-N-(2-(2-methoxyethoxy)-ethyl)-4-nitrosoaniline, N-(2-hydroxyethyl)-N-(3-methoxy-2-hydroxy-1-propyl)-4-nitrosoaniline, N-(2-hydroxyethyl)-N-(3-(2-hydroxyethoxy)-2-hydroxy-1-propyl)-4-nitrosoaniline, N-(2-hydroxyethyl)-N-(2-(2-hydroxyethoxy)-ethyl)-4-nitrosoaniline, 3-(4'-chloro-phenylimino)-3H-phenothiazine, 3-(4'-diethylamino-phenylimino)-3H-phenothiazine, 3-(4'ethyl-phenylimino)-3H-phenothiazine, 3-(4'-trifluoromethyl-phenylimino)-3H-phenothiazine, 3-(4'-methoxycarbonyl-phenylimino)-3H-phenothiazine, 3-(4'-nitro-phenylimino)-3H-phenothiazine, 3-(4'-methoxy-phenylimino)-3H-phenothiazine, 7-acetyl-3-(4'-methoxycarbonylphenylimino)-3H-phenothiazine, 7-trifluoromethyl-3-(4'-methoxycarbonylphenylimino)-3H-phenothiazine, 3-(4'-.omega.-carboxy-n-butyl-phenylimino)-3H-phenothiazine, 3-(4'-aminomethyl-phenylimino)-3H-phenothiazine, 3-(4'-(2"-(5"-(p-aminophenyl)-1,3,4-oxadiazoyl)phenylimino)-3H-phenothiazine, 3-(4'-β-aminoethyl-phenylimino)-3H-phenothiazine, 6-(4'-ethylphenyl)amino-3-(4'-ethyl-phenylimino)-3H-phenothiazine, 6-(4'-[2-(2-ethanoloxy)ethoxy]ethoxyphenyl)amino-3-(4'-[2-(2-ethanoloxy)ethoxy]ethoxy-phenylimino-3H-phenothiazine, 3-(4'-[2-(2-ethanoloxy)ethoxy]ethoxy-phenylimino-3H-phenothiazine, 3-(4'-phenylimino)-3H-phenothiazineboronic acid, (3-(3',5'-dicarboxy-phenylimino)-3H-phenothiazine, 3-(4'-carboxy-phenylimino)-3H-phenothiazine, 3-(3',5'-dicarboxy-phenylimino)-3H-phenoxazine, 3-(3',5'-phenylimino)-3H-phenothiazinedisulfonic acid, and 3-(3-phenylimino)-3H-phenothiazinesulfonic acid.

20. An electrochemical sensor for glucose in an aqueous sample, the sensor comprising a coplanar electrode system comprising a working electrode and a counter electrode, and a dried reagent composition covering at least a portion of the electrode system; where the dried reagent composition comprises (a) one or more enzymes selected from the group consisting of glucose dehydrogenases, glucose oxidoreductases, and combinations thereof (b) one or more mediators, mediator precursors, or a combination thereof, wherein at least one mediator or mediator precursor is aqueous soluble; (c) one or more zwitterionic buffers selected from the group consisting of 2-(N-morpholino) ethanesulfonic acid (MES), piperazine-N,N'-bis(2-ethanesulfonic acid) (PIPES), N-(2-Acetamido)-2-aminoethanesulfonic acid (ACES), (4-(2-hydroxyethyl)-1-piperazineethanesulfonic acid) (HEPES), N-(Tri(hydroxymethyl)methyl)glycine (tricine), N,N-Bis(2-hydroxyethyl)glycine; (bicine), 3-(N-morpholino)propanesulfonic acid (MOPS), N-cyclohexyl-3-aminopropanesulfonic acid (CAPS), N,N-Bis(2-hydroxyethyl)-2-aminoethanesulfonic Acid (BES), and N-(Hydroxyethyl)piperazine-N'-2-hydroxypropanesulfonic acid (HEPPSO); and (d) one or more thickeners; and where the sensor is configured for generating a current, and having a mean DC response loss of about 15% or less after storage for 4 weeks at 45° C. compared to storage for 4 weeks at 4° C.

\* \* \* \* \*